US006651649B2

(12) United States Patent
Spencer

(10) Patent No.: US 6,651,649 B2
(45) Date of Patent: Nov. 25, 2003

(54) METHOD AND DEVICE FOR TREATING EQUINE HERNIAS

(76) Inventor: Marjorie Ann Brown Spencer, 3194 Hillside Ave., Norco, CA (US) 92860

( * ) Notice: Subject to any disclaimer, the term of this patent is extended or adjusted under 35 U.S.C. 154(b) by 0 days.

(21) Appl. No.: 09/944,552

(22) Filed: Aug. 30, 2001

(65) Prior Publication Data

US 2003/0041858 A1 Mar. 6, 2003

(51) Int. Cl.[7] .......... A61F 5/24

(52) U.S. Cl. .......... 128/95.1; 119/856; 119/858; 119/907

(58) Field of Search .......... 128/95.1, 882; 602/23, 27, 62, 65, 75; 119/850, 856, 907, 725, 804, 858; 54/82

(56) References Cited

U.S. PATENT DOCUMENTS

| | | | | | |
|---|---|---|---|---|---|
| 2,825,330 | A | | 3/1958 | Storz | |
| 3,895,628 | A | * | 7/1975 | Adair | 602/79 |
| 3,920,008 | A | | 11/1975 | Lehman | |
| 4,351,325 | A | * | 9/1982 | Walker | |
| 4,355,600 | A | * | 10/1982 | Zielinski | 119/850 |
| 4,385,592 | A | * | 5/1983 | Goldstein | 602/18 |
| 4,671,264 | A | | 6/1987 | Frangi | |
| 4,787,379 | A | | 11/1988 | Yeh | |
| 5,105,806 | A | * | 4/1992 | Woodhouse et al. | 128/96.1 |
| 5,137,508 | A | | 8/1992 | Engman | |
| D330,273 | S | | 10/1992 | Cernek | |
| 5,259,397 | A | * | 11/1993 | McCabe | 128/897 |
| 5,323,790 | A | | 6/1994 | Guhle et al. | |
| 5,439,480 | A | | 8/1995 | Benckhuijsen | |
| 5,531,187 | A | * | 7/1996 | Ward | 119/856 |
| 5,624,391 | A | * | 4/1997 | Fan et al. | 602/63 |
| 5,662,640 | A | * | 9/1997 | Daniels | 604/392 |
| 5,823,984 | A | | 10/1998 | Silverberg | |
| 5,910,126 | A | | 6/1999 | Wilson et al. | |
| 5,941,199 | A | * | 8/1999 | Tamura | 119/850 |
| 5,996,537 | A | * | 12/1999 | Caditz | 119/850 |
| 6,112,704 | A | * | 9/2000 | Altafi | |
| 6,240,882 | B1 | | 6/2001 | Gross | |

* cited by examiner

*Primary Examiner*—Nicholas D. Lucchesi
*Assistant Examiner*—Lalita M. Hamilton
(74) *Attorney, Agent, or Firm*—Fulwider Patton Lee & Utecht, L.L.P.

(57) ABSTRACT

A device and method for treating equine hernia wherein a manipulator element is held in place to exert pressure on the affected abdomen to thereby push the bowel into the abdominal cavity. Any movements made by the horse, especially as by the act of walking or exercising, cause the manipulator element to shift slightly and thereby automatically manipulate the hernial ring. Such manipulation serves to expedite the healing process often obviating the need for surgical intervention.

16 Claims, 2 Drawing Sheets

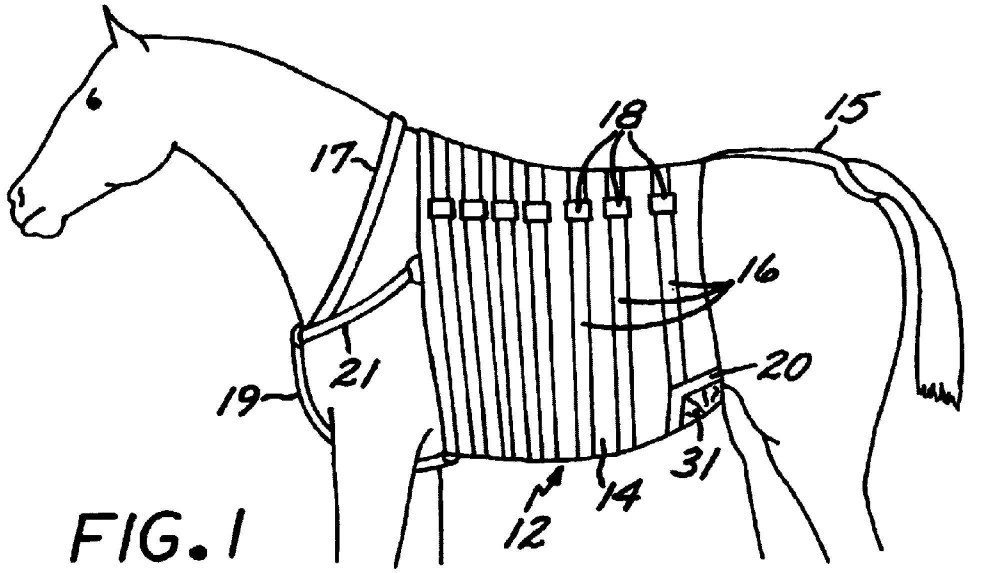
FIG. 1
FIG. 2
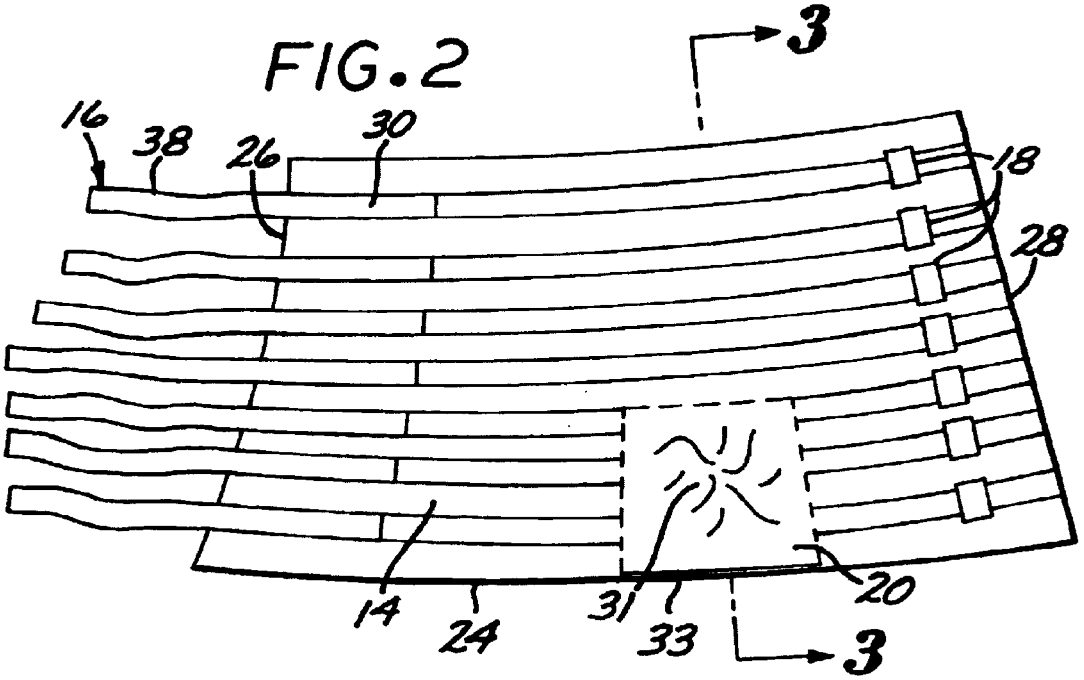

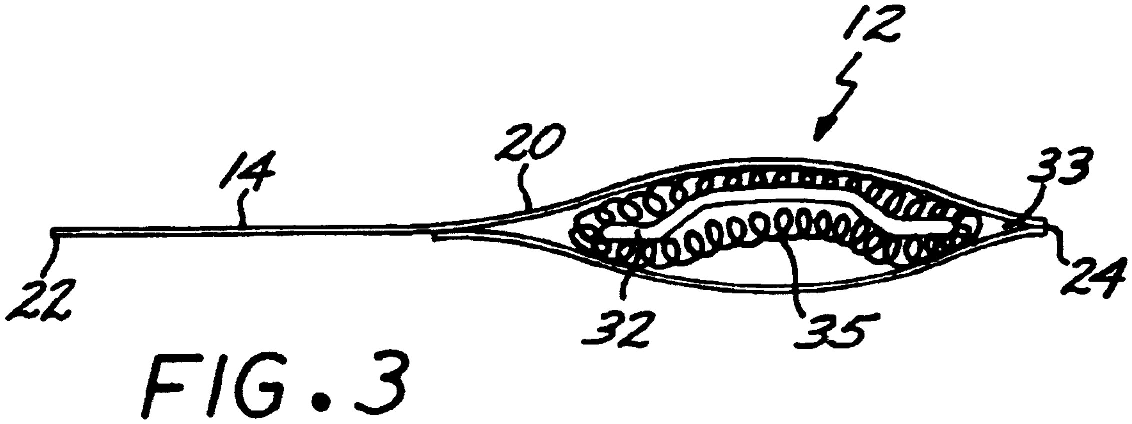
FIG. 3
FIG. 4
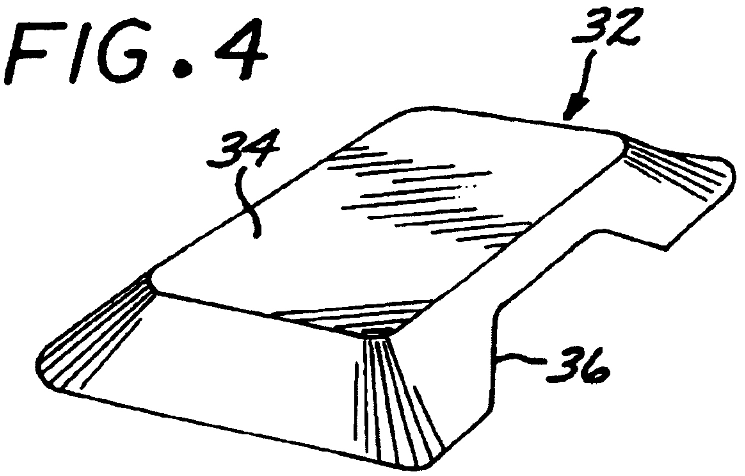

METHOD AND DEVICE FOR TREATING EQUINE HERNIAS

BACKGROUND OF THE INVENTION

The present invention generally relates to the treatment of equine hernias and more particularly pertains to a device and method that provides for the continuous and automatic manipulation of a hernia to promote healing.

Equines are fairly susceptible to hernias. Many such hernias are 'umbilical hernias' that are caused at birth such as when the mare rises too soon and thereby subjects the umbilical cord that is still attached to the foal to an excessive amount of tension. Such tension may cause a tear in the abdominal wall leaving only the skin covering the abdominal area to provide support. Hernias may additionally be caused by rearing, kicking, jumping or straining and are common to post-operative abdominal surgery. Ventral rupture may arise from an external injury. A hernia appears as a bulge in the animal's abdominal region which at the very least is considered unsightly and at worst may lead to complete failure of the abdominal wall and loss of all support for the intestines. The hernia may become strangulated which is a serious condition causing swelling, pain, hemorrhage, exudation, peritonitis and if not relieved, necrosis which can be fatal. Hernias are especially problematic in four-legged animals as the orientation of their abdominal region causes the entire weight of the intestines to be borne by the abdominal wall. This is further aggravated in horses in view of the immense size and weight of their intestines.

Surgery is common practice for the repair of equine hernias. In addition to the substantial cost involved, surgery always poses some degree of risk, including adverse reaction to anesthesia, infection as well as other potential complications along with an extended period of convalescence. Many heretofore employed methods for treating hernias in actuality merely amount to an effort to stabilize the herniation pending surgery by trussing or bandaging the region. While this typically prevents the hernia from increasing in size and may ease some of the discomfort that may be associated with the condition, it rarely if ever causes the hernia to heal or even shrink in size. The standard accepted method for the treatment of umbilical hernias in equine foals if the hernia is relatively small has been to wait until they are at least six months old to determine whether the hernia will heal on its own while optionally manipulating the hernia a few times a day during this period of time. Such manipulation includes applying pressure to the distended intestine so as to urge it back into the abdominal cavity while massaging the hernial ring in an effort to stimulate it to close. Some success can be realized with the massaging of the hernia. It has been theorized that such manipulation of the hernial ring actually induces the formation of new cell growth or scar tissue and the gradual tightening and closing of the ring. Additionally, the distended materials are forced back through the hernial ring and into the abdominal cavity to relieve some of the tension that the hernial ring is subjected to. The disadvantage associated with such approach is that the massaging sessions are time consuming and must be performed repeatedly. If by the sixth month the hernia has not healed, a clamp is attached to the skin where the hernia is located and tightened on a daily basis until the veterinarian determines the hernia to be ready for surgical repair. The clamp is painful to the foal and the entire approach is rather labor intensive insofar as daily attention is required.

An approach is needed for treating equine hernias that effectively promotes the healing rather than the mere stabilization of the hernia and that requires a minimal amount of expertise and effort to practice.

SUMMARY OF THE INVENTION

The present invention overcomes the shortcomings of the previously employed approaches for treating hernias in horses as well as other large four-legged animals. A non-invasive device and method are provided by which the hernia is automatically and continually manipulated to promote and expedite the healing process.

The method of the present invention provides for the continual and automatic manipulation of the hernia for an extended period of time. Pressure is focused on the herniated area while the precise positioning of the pressure within such area is subject to constant variation. In a preferred embodiment, the horse's own movements, especially the movements associated with walking, are relied upon to induce the slight shifting of the focus of pressure.

The device of the present invention consists of a relatively compliant support element that is adjustably fitted about the animal's abdomen wherein such element includes means for positioning a relatively rigid manipulator element directly over the hernia. The support element consists of a section of fabric configured to wrap around the animal's abdominal area and includes a series of straps to hold the fabric in place. The length of each of the straps is adjustable to allow the fabric to be tensioned to varying degrees and thereby tailored to a particular horse's needs. The manipulator element consists of a relatively stiff and hard mass of material which is positioned over the herniated region by the support element. The hard mass serves to focus pressure on the herniated intestines which not only serves to urge the herniated section of intestine back into the abdominal cavity, but tends to shift slightly whenever the animal moves and with each step as the animal walks. This constant shifting in effect causes the hernial ring to be continually manipulated which will eventually cause the hernial ring to close.

In a preferred embodiment, the manipulator element is held in a pocket formed in the support element. The size of the manipulator element and its shape may be tailored to suit the requirements of a particular patient. Various mechanisms may be employed to further stabilize the support element so as to keep it from shifting fore or aft along the horse's abdominal area. Hook and loop fasteners may be employed to seal the pocket and to facilitate adjustment of the support straps.

These and other features and advantages of the present invention will become apparent from the following detailed description of a preferred embodiment which, taken in conjunction with the accompanying drawings, illustrates by way of example the principles of the invention.

BRIEF DESCRIPTION OF THE DRAWINGS

FIG. 1 is a perspective view of the device of the present invention fitted about a horse;

FIG. 2 is a enlarged plan view of the device of the present invention laid out on a flat surface;

FIG. 3 is a further enlarged cross-sectional view taken along lines 3—3 of FIG. 2; and FIG. 4 is a perspective view of an embodiment of the manipulator element.

DETAILED DESCRIPTION OF THE PREFERRED EMBODIMENTS

The Figures generally show the device of the present invention. The device is fitted about a horse or other four legged animal suffering from a hernia and provides for the automatic and continual manipulation of the hernia. Walking or any other significant movement made by the animal will cause pressure focused by the device on the hernia to continually shift slightly thereby inducing a massaging action that has been found to be effective in expediting the healing process.

FIG. 1 shows the device 12 of the present invention fitted about a horse. The device generally consists of a generally rectangular support element 14 that includes a plurality of adjusting straps 16. The support element is dimensioned to fit about horse's entire torso and abdomen while the adjustment straps are of sufficient length to engage rectangular slides and allow for a range of adjustment. Any of a variety of securing mechanisms may alternatively be employed including for example a belt and buckle combination. A rectangular slide in combination with a hook and loop fastener is preferred due to its infinite adjustability and due to the fact that it can be quickly and easily fitted and adjusted. Additional straps may optionally be fitted to positively maintain the device in position, including for example a crupper 15 and/or various breast straps 17, 19, 21.

The support element 14 includes a pocket 20 formed therein configured for receiving a manipulator element therein. The pocket is oriented on the support element so as to allow a manipulator element contained therein to be positioned directly over the hernia. The pocket further provides for the manipulator element to be securely sealed therein yet allows for quick and easy access thereto.

FIG. 2 is an enlarged view of the device 12 of the present invention spread out on a flat surface. The support element 14 has a generally rectangular shape. A slightly trapezoidal shape may be desirable for some applications. The support element may be made of a fabric and has a leading edge 22, a trailing edge 24 and two lateral edges 26, 28. Extending from one lateral edge 26 is a series of straps 16. The straps may be attached to the entire width of the support element in order to enhance the support provided by the support element. Alternatively, a shorter section of strap may be attached to the support element. A section of hooks 38 and a section of loops 30 of a hook and loop fastener combination may be attached to the surface of the strap. In the preferred embodiment shown, the hook surface 38 is present near the distal end of each of the straps while a section of the complementing loop surface 30 is attached to each of the straps proximally thereto. A series of rectangular slides 18, configured to receive the straps 16, are attached to the support element adjacent the opposite lateral edge 28. The length of the distal ends of the straps is selected to extend from lateral edge 26, through the respective rectangular slide on the opposite lateral edge 28 and back so as to allow the hook surface 38 to engage the loop surface 30. Pocket 20 is positioned adjacent the trailing edge 24 of the support element. It is preferable that the pocket is offset with respect to the centerline of the device in order to ensure that the rectangular slides do not press on the horse's backbone when fitted. The pocket may be configured to open along the trailing edge where a hook and loop fastener 33 is fitted so as to allow a manipulator element to be accessibly retained within the pocket. The bulge 31 shown in the center of the pocket is formed by the manipulator element 32 contained therein in combination with a dense foam material 35 that surrounds the manipulator element to prevent damage to the skin caused by a concentration of pressure.

FIG. 3 is a cross-sectional view of the support element 14 showing the manipulator element 32 wrapped in a dense foam-like material 31 in place within pocket 20. The pocket is dimensioned to maintain the manipulator element therein in position. The manipulator element and foam-like material is easily removable through the opening formed along trailing edge 24. The opening is preferably sealed using a strip of hook and loop fastener 33.

FIG. 4 is an enlarged view of the manipulator element 32. The element is formed of a relatively rigid material such as a plastic and has a generally rectangular shape with rounded corners. The element includes a convex surface or dome 34, that may preferably be defined by a compound curve, to further serve to focus pressure applied therewith to the hernia. The manipulator element may optionally a cut-out section 36 for use on a male horse to avoid interference with the genitalia. While the dimensions of the manipulator element will be dictated by the size of the horse and hernia, a 4"×6" size would be required for a new born foal while a 6"×8" size may be required for a yearling. A dense foam-like material may additionally be disposed about the manipulator element to prevent damage to the surrounding skin.

The shape of the support element 14 and manipulator element 32 may have a slightly cut out configuration to accommodate the male equine genitalia. Additionally, because the various breeds differ slightly in shape and confirmation, attachments may be used to prevent the support element from shifting. A type of breast collar may be used to keep the device from moving aft on the male and a crupper strap may be used to keep the trailing edge from rolling over or twisting.

In use, a manipulator element 32 of the appropriate size is first selected to treat the particular herniation of a particular horse. The manipulator element is inserted into the pocket 20 of the support element 14 and the opening is sealed by aligning the hook and loop strips 30 fitted along the trailing edge of the pocket. The support element is then attached to the patient by maintaining the manipulator element directly over the hernia while tightening the adjustment straps. The tension in the straps must be adjusted to maintain the support element and manipulator element in position and such that the manipulator element focuses a sufficient amount of pressure on the hernia without causing undue discomfort to the horse. The device may be left in place around the clock but should be checked periodically to ensure the device is properly positioned and that no sores are being formed. Additionally, the condition of the hernia should be monitored periodically. It has been found that use of the device and method of the present invention can cause the hernia to heal within a matter of a few weeks.

While a particular form of the invention has been illustrated and described, it will also be apparent to those skilled in the art that various modifications can be made without departing from the spirit and scope of the invention. For example, the device can be adapted for use with any of a large number of similarly shaped animals that may suffer from hernias. The support element may also be used without the manipulator element as a post-surgical pressure bandage. Various adjustment mechanisms may be used to maintain the support element and manipulator element in place. Additionally, any of various materials may be used to form both the support element as well as the manipulator element. Finally, it is additionally contemplated that an active massaging device, such as a battery operated massager may be positioned within the pocket formed on the support element to further augment the massaging action generated by the animal's own movements. Accordingly, it is not intended that the invention be limited except by the appended claims.

What is claimed is:

1. A device for treating an abdominal hernia in an equine, comprising:

a resilient support element, dimensioned to cover and conform to the equine's abdominal area;

means for adjustably tensioning said support element about said equine's abdomen; and a less resilient, substantially non-conforming manipulator element, supported by said support element so as to be positioned directly over said hernia in said abdominal area and so as to shiftably focus pressure on said hernia.

2. The device of claim 1, wherein said means for adjustably tensioning said support element comprises adjustable straps dimensioned to extend over said equine's back.

3. The device of claim 1, wherein said support element has a pocket formed therein dimensioned to receive and retain said manipulator element.

4. The device of claim 1, wherein said manipulator element is supported such that said focus is subject to a slight shifting pursuant to certain movements made by said equine.

5. The device of claim 1, wherein said manipulator element comprises a mass of hard plastic.

6. The device of claim 1, wherein said manipulator element has a convex surface.

7. The device of claim 6, wherein said manipulator element has a generally rectangular shape.

8. The device of claim 1, wherein said support element has a pocket formed therein configured to receive and retain said manipulator element therein.

9. The device of claim 8, wherein said pocket is configured to removably receive and retain said manipulator element therein.

10. The device of claim 9, wherein said pocket has a reversibly sealable opening formed therein.

11. The device of claim 8, wherein said support element has a leading edge, a trailing edge and two lateral edges and wherein said pocket is formed along said trailing edge.

12. The device of claim 11, wherein said pocket has a sealable opening formed along said trailing edge of said support element.

13. The device of claim 1, wherein said support element is formed of a fabric material.

14. A method for non-invasively treating equine hernia, comprising the steps of:

fitting a resilient support element about said equine's abdominal region;

causing said resilient support element to maintain a non-resilient manipulator element in position directly over said hernia so as to shiftably focus pressure on said hernia; and relying on movements made by said equine to shift said focus of pressure on said hernia; and maintaining said manipulator element containing support element in place while said hernia heals.

15. The method of claim 14, further comprising the step of selecting a manipulator element having a convex surface.

16. The method of claim 14, further comprising the steps tensioning said support element about said equine's abdominal region so as to cause said manipulator element to exert pressure on said hernia.

* * * * *